United States Patent [19]
Wilson

[11] Patent Number: 5,902,844
[45] Date of Patent: May 11, 1999

[54] SPRAY DRYING OF PHARMACEUTICAL FORMULATIONS CONTAINING AMINO ACID-BASED MATERIALS

[75] Inventor: Edward S. Wilson, Wilmington, N.C.

[73] Assignee: Applied Analytical Industries, Inc., Wilmington, N.C.

[21] Appl. No.: 09/017,512

[22] Filed: Feb. 2, 1998

[51] Int. Cl.$^6$ ............... A61K 9/14; A61K 9/20; A61K 9/50
[52] U.S. Cl. ............... 524/17; 524/20; 524/21; 524/22; 524/23; 524/24; 524/25; 524/26; 424/464; 424/465; 424/484; 424/485; 424/486; 424/487; 424/489; 424/499
[58] Field of Search ............... 524/17, 20, 21, 524/22, 23, 24, 25, 26; 424/464, 465, 484, 485, 486, 487, 489, 499

[56] References Cited

U.S. PATENT DOCUMENTS

| | | | |
|---|---|---|---|
| 4,061,466 | 12/1977 | Sjoholm et al. | 23/230 |
| 4,205,128 | 5/1980 | Ishimatsu et al. | 435/182 |
| 4,272,620 | 6/1981 | Ichimura | 525/61 |
| 4,898,781 | 2/1990 | Onouchi et al. | 428/402.22 |
| 5,051,362 | 9/1991 | Suehiro | 435/182 |
| 5,330,767 | 7/1994 | Yamamoto et al. | 424/497 |

FOREIGN PATENT DOCUMENTS 0 501 375 A1  2/1992  European Pat. Off. .

OTHER PUBLICATIONS

Marco et al.; Feasibility Study on Spray–drying Protein Pharmaceuticals: recombinant human growth hormone and tissue–type plasminogen activator. (Abstract), Pharm. Res. 1994, 11(1), 12–20, (Eng.).

Gidwani et al.; Spray–dried enetric solid dispersion as a novel oral delivery system for a pentapeptide analog of thymopentin—BBS 92–13; (Abstract), Drug Development and Industrial Pharmacy, 18(4), Feb. 1992, pp. 385–394.

Mikhailova et al.; Conditions For The Drying Of The enzyme Preparation Pectomacerin; (Abstract), Biotekhnologiya, 1987, No. 4, pp. 473–477.

Daemen; The destruction of enzymes and backteria during the spray drying of milk and whey. A comparison of theoretrical computed results concerning the destruction of phosphatase with those obtained experimentally; (Abstract), Neth Milk Dairy J., 1984, 38(2), pp. 55–70.

Daemen; The destruction of enzymes and bateria during the spray–drying of milk whey. Analysis of the drying process according to the stages in which the destruction occurs; (Abstract), Neth MilkDairy J., 1983, 37(4), pp. 213–228.

Sultan et al.; Effects of supplemental protein source and alkaline hydrogen peroxide treatment of wheat straw on site of nutrient digestion and flow of nitrogenous compounds to the duodenum of steers; (Abstract), J. Anim. Sci., 70(12) Dec. 1992, pp. 3909–3915.

Ulloa et al.; Obtention of a protein concentrate of chickpea (*Cicer arietinum*) by ultrafiltration; (Abstract), Arch Latinoam Nutr., 41(4) Dec. 1991, pp. 595–608.

Rudolph et al.; Solubility and digestibility of milk proteins in infant formulas exposed to different heat treatments; (Abstract), J. Pediatr. Gastroenterol Nutr. 15(1), Jul. 1992, pp. 25–33.

Mumenthaler et al., Feasibility Study on Spray–Drying Protein Pharmaceuticals: Recombinant Human Growth Hormone and Tissue–Type Plasminogen Activator, Pharmaceutical Research, vol. 11, No. 1, pp. 12–20 (1994).

Mumenthaler et al., Preparation of Protein Pharmaceuticlas Using a Spray–Drying Technique, Pharmaceutical Research (NY), vol. 8, No. 10 (Supp) (1991) (Abstract).

Gombotz et al.; The Stabilization of a Human IgM Monoclonal Antibody with Poly(vinylpyrrolidone); *Pharmaceutical Research*; vol. 11, No. 5 (1994).

*Primary Examiner*—Nathan M. Nutter
*Attorney, Agent, or Firm*—Myers Bigel Sibley & Sajovec

[57] ABSTRACT

Methods of forming solid pharmaceutical compositions comprise solubilizing water-soluble polymers and amino acid-based components having molecular weights ranging from about 100 daltons to about 200,000 daltons or pharmaceutically acceptable salts thereof in solvents; and separating the solvents from the water-soluble polymers and the amino acid-based components or pharmaceutically acceptable salts thereof to form solid pharmaceutical compositions comprising the water-soluble polymers and the amino acid-based components or pharmaceutically acceptable salts thereof.

12 Claims, No Drawings

1

SPRAY DRYING OF PHARMACEUTICAL FORMULATIONS CONTAINING AMINO ACID-BASED MATERIALS

FIELD AND BACKGROUND OF THE INVENTION

The present invention generally relates to pharmaceutical compositions and methods of making the same.

Amino acid-based materials, particularly high molecular weight amino acid-based materials such as peptides, proteins, and enzymes, are known to be useful in a number of therapeutic indications. For example, materials such as somatostatin and somatotropin are typically employed as growth hormone regulators. Additionally, somatostatin may be used in the treatment of hemorrhage of gastro-duodenal ulcers.

Traditionally, formulations containing these materials have been formed by various freeze-drying techniques. A solution containing an amino acid-based material is typically loaded into containers (e.g., vials) and the temperatures of the solutions are lowered until it is frozen. These temperatures may reach as low as −60° C. The temperature of the solutions are then slowly raised, typically over the course of a number of days until the diluent is sublimed out under high vacuum, and the desired composition is obtained. The final composition is typically present in the form of a dried powder.

Notwithstanding any potential advantages, the above process suffers from various drawbacks. The freeze drying process is typically time consuming, tedious, and expensive in that it involves multiple steps over a prolonged period of time. Additionally, the processing equipment can limit the production batch size to what can fit into the lyophilizer. Moreover, the final product in the form of a dried powder comprising the peptides, enzymes, or proteins often must be maintained in a reduced temperature environment in order for the pharmaceutical materials to remain stable.

A method for forming immobilized enzymes by using a spray drying process is proposed in U.S. Pat. No. 5,051,362 to Soehiro. A given enzyme is disclosed to be dissolved in an aqueous solution of styrylpyridinium group- or styrylquinolinium group-containing poly(vinyl alcohol). The enzyme-containing aqueous solution is then spray dried, and the resulting dry particles are subsequently subjected to a photo-crosslinking step. The '362 patent may be considered disadvantageous because it requires using a specifically-tailored solvent material, namely the modified poly(vinyl alcohol). Moreover, the use of photo-crosslinking involves an additional operation which adds time and expense to the above process.

Thus, there is a need in the art for a process for producing amino acid-based materials which is more efficient than current conventional processes. For example, it would be advantageous if the process did not require a photo-crosslinking step. It would be desirable if such a process could utilize existing solvents, buffers, and the like. It would also be desirable to be able to produce large quantities of drug/drug product in one batch or a continuous process operation. Additionally, the ability to stabilize the amino acid-based materials in dry form without the need for refrigeration would be desirable.

SUMMARY OF THE INVENTION

It is therefore an object of the present invention to provide processes for producing solid compositions containing amino acid-based materials which are more efficient than conventional processes (e.g., does not require photo-crosslinking).

It is another object of the invention to provide processes for producing solid compositions containing amino acid-based materials which can use existing solvents, buffers, etc.

It is yet another object of the invention to provide processes for producing solid compositions containing amino acid-based materials in large quantities utilizing batch or continuous operations.

It is another object of the invention to produce solid compositions containing amino acid-based materials such that the resulting materials do not need to be refrigerated.

To these objects and others, in one aspect the invention provides methods of forming solid pharmaceutical compositions. The methods comprise solubilizing water-soluble polymers and amino acid-based components or pharmaceutically acceptable salts thereof in solvents to form solubilized mixtures. The amino acid-based components have molecular weights ranging from about 100 daltons to about 200,000 daltons. The solvents are then separated from the water-soluble polymers and the amino acid-based components or pharmaceutically acceptable salts thereof to form solid pharmaceutical compositions comprising the water-soluble polymers and the amino acid-based components or pharmaceutically acceptable salts thereof.

In another aspect, the invention provides solid pharmaceutical compositions. The solid pharmaceutical compositions comprise amino acid-based components having molecular weights ranging from about 100 daltons to about 200,000 daltons or pharmaceutically acceptable salts thereof, and water-soluble polymers. In accordance with the invention, the water-soluble polymers support and stabilize the amino acid-based components or pharmaceutically acceptable salts thereof.

DETAILED DESCRIPTION OF THE PREFERRED EMBODIMENTS

The invention will now be described in greater detail with reference to its preferred embodiments. These embodiments, however, are set forth to illustrate the invention and are not to be construed as a limitation thereof.

The invention relates to a method of forming a solid pharmaceutical compositions. The method comprises solubilizing at least one water-soluble polymer and at least one amino acid-based component having a molecular weight ranging from about 100 daltons to about 200,000 daltons, or a pharmaceutically acceptable salt thereof, in a solvent to form a solubilized mixture. Examples of solvents which may be used include, but are not limited to, water or an alcohol/water mixture. The solvent is then separated from the water-soluble polymer and the amino acid-based component, or pharmaceutically acceptable salt thereof, to form a solid pharmaceutical composition. The solid pharmaceutical composition comprises: (i) at least one amino acid-based component or pharmaceutically acceptable salt thereof; and (ii) at least one water-soluble polymer. The solid pharmaceutical composition typically has a moisture content which is less than or no greater than 25 weight percent, more preferably less than or no greater than about 15 weight percent. The composition is preferably in the form of a spray dried powder having an average particle size ranging from about 0.1 μm to about 100 μm.

For the purposes of the invention, the term "amino acid-based component" should be broadly construed to include various amino acid-containing materials such as, but not limited to, peptides, proteins, enzymes, and the like. Examples of peptide components include, but are not limited to, gonadorelin acetate, chorionic gonadotropin, somatropin, altepase, calcitonic, somatostatin, vasopressin, glucagon, menotropins, urofollitropin, somatoprem, α-galactosidase, β-galactosidase, and mixtures thereof. In particular, the α-galactosidase and the β-galactosidase preferably have molecular weights of about 135,000 daltons, and typically contain about 500 residues of arginine and lysine and 96 residues of methionine (see K. Wallenfels and R. Weil, *Enzymes*, Chapter 20, Vol. 7, Boyer Acadmeic Press, $3^{rd}$ Ed., pp. 617–663). Other examples of molecular weights of proteins are as follows: vasopresin (9 amino acids) 1084 daltons, and glucagon (29 amino acids) 3,483, IgG ~55,000 daltons. In general, the amino acid-based component has a most preferred molecular weight ranging from about 1000 daltons to about 140,000 daltons.

As described herein, pharmaceutically acceptable salts of the amino acid-based components may also be employed. To illustrate, the salts are preferably formed by employing an organic or inorganic base. Examples of suitable bases for salt formation include compounds containing alkali metals or alkali earth metals, although it is appreciated by the skilled artisan that bases containing other types of metals may be used. Examples of inorganic bases include, but are not limited to, sodium hydroxide, sodium carbonate, sodium bicarbonate, potassium hydroxide, calcium hydroxide, and the like. Organic bases in the form of, for example, nitrogen-containing components may be also used such as, for example, ammonia, organic amines, and the like. Mixtures of the above may be used. The salts may be formed by reacting the amino acid-based component with an appropriate amount of the desired base in a manner known to those who are skilled in the art.

The amino acid-based component or pharmaceutically acceptable salt thereof may be present in the solid pharmaceutical composition in various amounts. Preferably, the solid pharmaceutical composition comprises from about 1 to about 75 percent by weight of this component, and more preferably from about 5 to about 50 percent by weight.

A wide range of water-soluble polymers may be used in the solid pharmaceutical composition of the invention. Examples of water-soluble polymers include, but are not limited to, poly(vinylpyrrolidone), hydroxypropyl methylcellulose, hydroxypropyl cellulose, carbomer, alginates, colloidal magnesium aluminum silicates, ethyl cellulose, polyethylene oxides, and the like. Mixtures thereof may also be used. Various amounts of a water-soluble polymer may be used in the solid pharmaceutical composition of the invention. Preferably, the solid pharmaceutical composition comprises from about 10 to about 90 percent by weight of a water soluble polymer, and more preferably from about 50 to about 90 percent by weight.

The invention also encompasses an embodiment in which the solid pharmaceutical composition further comprises a pharmaceutically acceptable carrier, diluent, or excipient, the selection of which are known to the skilled artisan. In making these formulations, the solid pharmaceutical composition is usually mixed with an excipient, diluted by an excipient or enclosed within such a carrier which can be in the form of a capsule, sachet, tablet, paper, or other container. When the excipient serves as a diluent, it may be a solid, semi-solid, or liquid material which acts as a vehicle, carrier, or medium for the amino acid-based component or pharmaceutically acceptable salt thereof. Thus, the formulations can be in the form of tablets, pills, powders, elixirs, suspensions, emulsions, solutions, syrups, soft and hard gelatin capsules, suppositories, sterile injectable solutions, and sterile packaged powders.

Examples of suitable excipients include, but are not limited to, starches, gum acacia, calcium silicate, microcrystalline cellulose, polyvinylpyrrolidone, cellulose, water, syrup, and methyl cellulose. The formulations can additionally include lubricating agents such as talc, magnesium stearate and mineral oil; wetting agents; emulsifying and suspending agents; preserving agents such as methyl- and propylhy-droxybenzoates; sweetening agents; or flavoring agents. Polyols, buffers, and inert fillers may also be used. Examples of polyols include, but are not limited to, mannitol, sorbitol, xylitol, sucrose, maltose, glucose, lactose, dextrose, and the like. Suitable buffers encompass, but are not limited to, phosphate, citrate, tartarate, succinate, and the like. Other inert fillers which may be used encompass those which are known in the art and are useful in the manufacture of peptide component dosage forms. If desired, the solid pharmaceutical compositions may include other components such as bulking agents and/or granulating agents, and the like. The compositions of the invention can be formulated so as to provide quick, sustained, or delayed release of the active ingredient after administration to the patient by employing procedures well known in the art.

In the event that the above formulations are to be used for parenteral administration, such a formulation typically comprises sterile aqueous and non-aqueous injection solutions comprising the amino acid-based components or pharmaceutically acceptable salts thereof, which preparations are preferably isotonic with the blood of the intended recipient. These preparations may contain anti-oxidants, buffers, bacteriostats, and solutes which render the formulation isotonic with the blood of the intended recipient. Aqueous and non-aqueous sterile suspensions may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

Referring now to the methods of the invention, the separation of the water-soluble polymers and the amino acid-based components are preferably carried out by first dispersing the solubilized mixtures, and then exposing the solvents to the gaseous streams such that the solvents separate from the water-soluble polymers and amino acid-based components. The gaseous streams may comprise a variety of components such as, but not limited to, air, nitrogen, argon, and other inert substances, the selection of which are known in the art. In these embodiments, the gaseous stream may be employed under various conditions. For example, the gaseous streams are typically utilized at temperatures ranging from about 20° C. to about 140° C., and more preferably from about 90° C. to about 120° C.

The spray drying techniques which are used in the invention are known to those skilled in the art. An example of such a technique is described in U.S. Pat. No. 5,051,362 to Suehiro et al., the disclosure of which is incorporated by reference herein in its entirety. A number of spray dryers may be used, the selection of which are known by one skilled in the art. Examples of spray dryers include, but are not limited to, two-fluid nozzle, airless spray, rotary disk type spray, and the like. In general, the selection of the spray drier components and operating parameters can be made so as to regulate the diameter of the resulting droplets if desired.

According to the spray drying processes of the invention, buffered solutions are prepared and water-soluble polymers are dissolved therein. Subsequently, amino acid-based materials are charged to the above solutions, and the ingredients are typically agitated until thoroughly mixed. Other ingredients alluded to herein may also be added to these solutions. The mixtures are then sprayed in gaseous streams. The initial temperature of the gaseous stream used in the spray drying processes may be selected among various values. For example, the gas currents may be maintained at temperature such that the amino acid-based materials do not undergo an appreciable level of thermal degradation. The sprayed materials which are generated may then be collected, e.g., by a cyclone to form the solid pharmaceutical compositions of the invention. The drying typically takes place in an expansion chamber. The resulting solid pharmaceutical compositions may then be further processed according to techniques known to the skilled artisan.

Advantageously, the methods of the invention are more efficient than conventional methods in that photo-crosslinking steps are not required. Moreover, the water-soluble polymers support and stabilize the amino acid-based components such that the solid pharmaceutical compositions do not need to be subjected to temperatures lower than ambient, unlike conventional compositions.

The following examples are set forth to illustrate the present invention, and should not be construed as limiting thereof.

EXAMPLE 1

Buffer Preparation

A buffer was prepared by charging 69 ml of 1N sodium hydroxide solution (40 g/1000 ml) to 1000 ml of 0.1M potassium phosphate monobasic solution (13.6 g/1000 ml). The mixture was agitated until uniform. The pH of the mixture was adjusted to 7.0 by adding phosphoric acid. 60.4 mg of magnesium sulfate was charged and dissolved in the mixture. Subsequently, 12.6 mg of magnesium chloride was charged and dissolved in the mixture.

EXAMPLE 2

Buffer Preparation

A buffer was prepared by charging 2.56 g of sodium acetate, 30.2 mg magnesium sulfate, and 6.3 mg magnesium chloride to 400 ml of milli-q water in a 500 ml volumetric flask. The pH of the mixture was adjusted to 5.8 by adding 0.5N HCl to the mixture. The mixture volume was raised to 500 ml by adding water, and the mixture was agitated until uniform.

EXAMPLE 3

Product Solution Preparation and Spray Drying 40 g of PVP was charged and dissolved in 160 g of the potassium phosphate buffer prepared in Example 1. 10 g of lactase liquid was charged and dispersed to the PVP/potassium phosphate solution, and the resulting mixture was gently mixed.

The solution was then spray dried by using a Yamato-Pulvis Mini Spray Dryer Model No. GA-31. The following parameters were employed:

| | |
|---|---|
| inlet temp. | 90° C.–100° C. |
| outlet temp. | 25° C.–30° C. |
| atomization | 1.6–2.0 |
| pump rate | 1.8 |
| aspirator | 6.5–8.5 |

EXAMPLE 4

Product Solution Preparation and Spray Drying 40 g of PVP was charged and dissolved in 160 g of the acetate buffer prepared in Example 2. 10 g of Beano™ liquid was charged and dispersed to the PVP/acetate buffer solution, and the resulting mixture was gently mixed.

The solution was then spray dried by using a Yamato-Pulvis Mini Spray Dryer Model No. GA-31. The following parameters were employed

| | |
|---|---|
| inlet temp. | 90° C.–100° C. |
| outlet temp. | 60° C.–65° C. |
| atomization | 1.5 |
| pump rate | 1.8 |
| aspirator | 7.0 |

The compositions described in Examples 3 and 4 are set forth in Table 1. Table 2 shows actual potency values for these materials and compares them with the theoretical potencies. As illustrated, the materials display good actual potency values.

TABLE 1

Composition of Formulations

| Ingredients | Example 3 | Example 4 |
|---|---|---|
| Lactase Liquid (Maxilact LX5000 #5135) | 10.0 g | — |
| Beand ™ Liquid | — | 10.0 g |
| Povidone (K28/32) | 40.0 g | 20.0 g |
| Maltodextrin | — | — |
| Methocel (E15LV) | — | — |
| Cab-o-sil | — | — |
| Sodium Hydroxide | 413.17 mg | — |
| Potassium Phosphate Monobasic | 90.85 mg | — |
| Magnesium Sulfate | 9.04 mg | 9.66 mg |
| Manganese Chloride | 1.89 mg | 2.02 mg |
| Sodium Acetate | — | 819.0 mg |
| Phosphoric acid to pH 7.0 | 15 drops | 0.13 ml |
| Hydrochloric acid to pH 5.8 | — | 0.13 ml |

TABLE 2

Potencies of Spray Dried Formulations

| Product | Example | Theoretical Potency | Actual Potency | % Label Claim |
|---|---|---|---|---|
| Spray Dried Lactase | 3 | 1234 NLU/g | 967.6 NLU/g | 78.4 |
| Spray Dried Beano ™ | 4 | 14.45 units/g | 21.0 units/g | 145.5 |

The preferred embodiments and examples described in the specification have been set forth to illustrate the invention. The scope of the invention, however, is defined by the foregoing claims.

That which is claimed:

1. A method of forming a solid pharmaceutical composition, said method comprising:

solubilizing at least one water-soluble polymer and at least one amino acid-based containing component having a molecular weight ranging from about 100 daltons to about 200,000 daltons, or a pharmaceutically acceptable salt thereof, in an aqueous solvent to form a solubilized mixture; and separating the aqueous solvent from the at least one water-soluble polymer and the at least one amino acid-containing component, or pharmaceutically acceptable salt thereof, to form a solid pharmaceutical composition comprising the at least one water-soluble polymer and the at least one amino acid-containing component or pharmaceutically acceptable salt thereof.

2. The method according to claim 1, wherein the solvent is selected from the group consisting of water and an alcohol/water mixture.

3. The method according to claim 1, wherein the at least one amino acid-based component component is selected from the group consisting of gonadorelin acetate, chorinic gonadotropin, somatropin, altepase, calcitonic, somatostatin, vasopressin, glucagon, menotropins, urofollitropin, somatoprem, α-galactosidase, β-galactosidase, and mixtures thereof.

4. The method according to claim 1, wherein said step of separating the solvent from the at least one water-soluble polymer and the at least one amino acid-based component or pharmaceutically acceptable salt thereof comprises:

dispersing the solubilized mixture; and exposing the solubilized mixture to a gaseous stream such that the solvent separates from the at least one amino acid-based component or pharmaceutically acceptable salt thereof and the at least one water-soluble polymer.

5. The method according to claim 4, wherein the gaseous stream is present at a temperature ranging from about 20° C. to about 140° C.

6. The method according to claim 4, wherein the gaseous stream comprises a component selected from the group consisting of air, nitrogen, argon, and mixtures thereof.

7. The method according to claim 1, wherein the at least one water-soluble polymer is selected from the group consisting of poly(vinylpyrrolidone), hydroxypropyl methylcellulose, hydroxypropyl cellulose, carbomer, alginates, colloidal magnesium aluminum silicates, ethyl cellulose, polyethylene oxides, and mixtures thereof.

8. The method according to claim 7, wherein the solvent is selected from the group consisting of water and an alcohol/water mixture.

9. The method according to claim 8, wherein the at least one amino acid-based component component is selected from the group consisting of gonadorelin acetate, chorinic gonadotropin, somatropin, altepase, calcitonic, somatostatin, vasopressin, glucagon, menotropins, urofollitropin, somatoprem, α-galactosidase, β-galactosidase, and mixtures thereof.

10. The method according to claim 9, wherein said step of separating the solvent from the at least one water-soluble polymer and the at least one amino acid-based component or pharmaceutically acceptable salt thereof comprises:

dispersing the solubilized mixture; and exposing the solubilized mixture to a gaseous stream such that the solvent separates from the at least one amino acid-based component or pharmaceutically acceptable salt thereof and the at least one water-soluble polymer.

11. The method according to claim 10, wherein the gaseous stream is present at a temperature ranging from about 20° C. to about 140° C.

12. The method according to claim 11, wherein the gaseous stream comprises a component selected from the group consisting of air, nitrogen, argon, and mixtures thereof.

* * * * *

UNITED STATES PATENT AND TRADEMARK OFFICE
CERTIFICATE OF CORRECTION

PATENT NO. : 5,902,844
DATED : May 11, 1999
INVENTOR(S) : Edward S. Wilson

It is certified that error appears in the above-identified patent and that said Letters Patent is hereby corrected as shown below:

Col. 6, Line 39 delete "Beand" and insert --Beano--.

Col. 7, Line 2 delete "-based".

Col. 8, Line 14, after "component" delete "component".

Signed and Sealed this

Fifth Day of September, 2000

Attest:

Q. TODD DICKINSON

*Attesting Officer*    *Director of Patents and Trademarks*